US010376192B2

(12) United States Patent
Lee et al.

(10) Patent No.: US 10,376,192 B2
(45) Date of Patent: Aug. 13, 2019

(54) SYSTEM AND METHOD FOR CONTACTLESS BLOOD PRESSURE DETERMINATION

(71) Applicant: NURALOGIX CORPORATION, Toronto (CA)

(72) Inventors: Kang Lee, Toronto (CA); Evgueni Kabakov, North York (CA); Phil Levy, Brampton (CA)

(73) Assignee: NURALOGIX CORPORATION, Toronto, Ontario (CA)

( * ) Notice: Subject to any disclaimer, the term of this patent is extended or adjusted under 35 U.S.C. 154(b) by 0 days.

(21) Appl. No.: 15/923,225

(22) Filed: Mar. 16, 2018

(65) Prior Publication Data

US 2018/0199870 A1 Jul. 19, 2018

Related U.S. Application Data

(63) Continuation of application No. PCT/CA2017/051533, filed on Dec. 19, 2017.

(Continued)

(51) Int. Cl.

*A61B 5/1455* (2006.01)
*A61B 5/00* (2006.01)

(Continued)

(52) U.S. Cl.

CPC .......... *A61B 5/14551* (2013.01); *A61B 5/021* (2013.01); *A61B 5/0205* (2013.01);

(Continued)

(58) Field of Classification Search

CPC ....... A61B 5/0205; A61B 5/021; A61B 5/026; A61B 5/145; A61B 5/1455;

(Continued)

(56) References Cited

U.S. PATENT DOCUMENTS

| | | | | | |
|---|---|---|---|---|---|
| 7,610,166 | B1 * | 10/2009 | Solinsky | G01C 21/005 | 702/141 |
| 2013/0197377 | A1 * | 8/2013 | Kishi | A61B 5/721 | 600/508 |
| 2016/0098592 | A1 * | 4/2016 | Lee | G06F 19/321 | 434/236 |

FOREIGN PATENT DOCUMENTS

| | | | |
|---|---|---|---|
| WO | 2016037033 A1 | | 3/2016 |
| WO | WO 2016/037033 A1 | * | 3/2016 |

OTHER PUBLICATIONS

Jain et al, "Face Video Based Touchless Blood Pressure and Heart Rate Estimation", Sep. 2016, IEEE, pp. 1-5 (Year: 2016).*

(Continued)

*Primary Examiner* — Edward Park
(74) *Attorney, Agent, or Firm* — Marc Lampert; Anil Bhole; Bhole IP Law

(57) ABSTRACT

A system and method for contactless blood pressure determination. The method includes: receiving a captured image sequence; determining, using a trained hemoglobin concentration (HC) changes machine learning model, bit values from a set of bitplanes in the captured image sequence that represent the HC changes of the subject; determining a blood flow data signal; extracting one or more domain knowledge signals associated with the determination of blood pressure; building a trained blood pressure machine learning model with a blood pressure training set, the blood pressure training set including the blood flow data signal of the one or more predetermined ROIs and the one or more domain knowledge signals; determining, using the blood pressure machine learning model trained with a blood pressure training set, an estimation of blood pressure; and outputting the determination of blood pressure.

28 Claims, 9 Drawing Sheets

Related U.S. Application Data

(60) Provisional application No. 62/435,942, filed on Dec. 19, 2016.

(51) Int. Cl.

| | |
|---|---|
| ***A61B 5/021*** | (2006.01) |
| ***A61B 5/0205*** | (2006.01) |
| ***A61B 5/026*** | (2006.01) |
| ***A61B 5/145*** | (2006.01) |
| ***G16H 50/20*** | (2018.01) |
| ***G16H 40/63*** | (2018.01) |
| ***G16H 50/30*** | (2018.01) |
| *A61B 5/08* | (2006.01) |
| *A61B 5/024* | (2006.01) |

(52) U.S. Cl.

CPC .............. *A61B 5/026* (2013.01); *A61B 5/145* (2013.01); *A61B 5/1455* (2013.01); *A61B 5/725* (2013.01); *A61B 5/7267* (2013.01); *A61B 5/7278* (2013.01); *G16H 40/63* (2018.01); *G16H 50/20* (2018.01); *G16H 50/30* (2018.01); *A61B 5/0037* (2013.01); *A61B 5/024* (2013.01); *A61B 5/0261* (2013.01); *A61B 5/0816* (2013.01)

(58) Field of Classification Search

CPC ... A61B 5/14551; A61B 5/725; A61B 5/7267; A61B 5/7278; A61B 5/0037; A61B 5/024; A61B 5/0261; A61B 5/0816; G16H 40/63; G16H 50/20; G16H 50/30

See application file for complete search history.

(56) References Cited

OTHER PUBLICATIONS

Xing et al, "Optical blood pressure estimation with photoplethysmography and FFT-based neural networks", Jul. 2016, OSA, pp. 1-14 (Year: 2016).*

International Search Report corresponding to PCT/CA2017/051533; Canadian Intellectual Property Office; dated Feb. 20, 2018.

Written Opinion of the International Searching Authority corresponding to PCT/CA2017/051533; Canadian Intellectual Property Office; dated Feb. 20, 2018.

Jain, M. et al., "Face video based touchless blood pressure and heart rate estimation." IEEE 18th International Workshop on Multimedia Signal Processing (MMSP), Sep. 23, 2016 (Sep. 23, 2016).

Xing X. et al., "Optical blood pressure estimation with photoplethysmography and FFT-based neural networks", Biomedical optics express. vol. 7(8), Aug. 1, 2016 (Aug. 1, 2016, pp. 3007-3020.

* cited by examiner

SYSTEM AND METHOD FOR CONTACTLESS BLOOD PRESSURE DETERMINATION

TECHNICAL FIELD

The following relates generally to detection of a human blood pressure and more specifically to a system and method for contactless human blood pressure determination, via a data-driven and machine learning approach.

BACKGROUND

Measurement of blood pressure is the primary approach used to diagnose conditions such as hypertension. Conventionally, arterial pressures of the human circulatory system are measured through invasive means, for example, by penetrating the skin and taking pressure measurements from within the blood vessels, such as with intra-arterial techniques; or by non-invasive means, which provide an estimate of the actual pressure. The former approach is typically restricted to highly qualified and trained staff that monitor arterial lines on patients at intensive care centres within a hospital setting. The latter approach typically includes non-invasive techniques seen in general practice for routine examinations and monitoring. An exemplary arterial pressure waveform signal measured from an inter-arterial blood pressure monitor, including some of the associated features of the signal, is shown in FIG. 7.

As an example, two currently popular conventional approaches for conducting Non-Invasive Blood Pressure (NIBP) measurements both require direct physical contact to be established between an instrument and a human subject.

One of the conventional approaches, an auscultatory approach, uses a stethoscope and a sphygmomanometer. This approach includes an inflatable cuff placed around the upper arm at roughly the same vertical height as the heart, attached to a mercury or aneroid manometer.

The second of the conventional approaches, an oscillometric approach, is functionally similar to that of the auscultatory method, but with an electronic pressure sensor (transducer) fitted in the cuff to detect blood flow, instead of using the stethoscope and an expert's judgment. In practice, the pressure sensor is a calibrated electronic device with a numerical readout of blood pressure. To maintain accuracy, calibration must be checked periodically, unlike with the mercury manometer. In most cases, the cuff is inflated and released by an electrically operated pump and valve, which may be fitted on the wrist (elevated to heart height) or other area. The oscillometric method can vary widely in accuracy, and typically needs to be checked at specified intervals, and if necessary recalibrated.

Thus, conventional approaches require close access and direct physical contact with a human subject's body, typically with the arm of the subject. This contact requires that the subject is compliant and aware that a blood pressure measurement is underway. As an example, to acquire a subject's blood pressure, they must have knowledge of the measurement and be physically collocated with the NIBP instrument.

SUMMARY

In an aspect, there is provided a method for contactless blood pressure determination of a human subject, the method executed on one or more processors, the method comprising: receiving a captured image sequence of light re-emitted from the skin of one or more humans; determining, using a trained hemoglobin concentration (HC) changes machine learning model trained with a HC changes training set, bit values from a set of bitplanes in the captured image sequence that represent the HC changes of the subject, the HC changes training set comprising the captured image sequence; determining a blood flow data signal of one or more predetermined regions of interest (ROIs) of the subject captured on the images based on the bit values from the set of bitplanes that represent the HC changes; extracting one or more domain knowledge signals associated with the determination of blood pressure from the blood flow data signal of each of the ROIs; building a trained blood pressure machine learning model with a blood pressure training set, the blood pressure training set comprising the blood flow data signal of the one or more predetermined ROIs and the one or more domain knowledge signals; determining, using the blood pressure machine learning model trained with the blood pressure training set, an estimation of blood pressure for the human subject; and outputting the determination of blood pressure.

In a particular case, determining the estimation of blood pressure comprises determining an estimation of systolic blood pressure (SBP) and diastolic blood pressure (DBP).

In another case, the set of bitplanes in the captured image sequence that represent the HC changes of the subject are the bitplanes that are determined to significantly increase a signal-to-noise ratio (SNR).

In yet another case, the method further comprising pre-processing the blood flow data signal with a Butterworth filter or a Chebyshev filter.

In yet another case, extracting the one or more domain knowledge signals comprises determining a magnitude profile of the blood flow data signal of each of the ROIs.

In yet another case, determining the magnitude profile comprises using digital filters to create a plurality of frequency filtered signals of the blood flow data signal in the time-domain for each image in the captured image sequence.

In yet another case, extracting the one or more domain knowledge signals comprises determining a phase profile of the blood flow data signal of each of the ROIs.

In yet another case, determining the phase profile comprises: applying a multiplier junction to the phase profile to generate a multiplied phase profile; and applying a low pass filter to the multiplied phase profile to generate a filtered phase profile.

In yet another case, determining the phase profile comprises determining a beat profile, the beat profile comprising a plurality of beat signals based on a Doppler or an interference effect.

In yet another case, extracting the one or more domain knowledge signals comprises determining at least one of systolic uptake, peak systolic pressure, systolic decline, dicrotic notch, and diastolic runoff of the blood flow data signal of each of the ROIs.

In yet another case, extracting the one or more domain knowledge signals comprises determining waveform morphology features of the blood flow data signal of each of the ROIs.

In yet another case, extracting the one or more domain knowledge signals comprises determining one or more biosignals, the biosignals comprising at least one of heart rate measured from the human subject, Mayer waves measured from the human subject, and breathing rates measured from the human subject.

In yet another case, the method further comprising receiving ground truth blood pressure data, and wherein the blood pressure training set further comprises the ground truth blood pressure data.

In yet another case, the ground truth blood pressure data comprises at least one of an intra-arterial blood pressure measurement of the human subject, an auscultatory measurement of the human subject, or an oscillometric measurement of the human subject.

In yet another case, the method further comprising applying a plurality of band-pass filters, each having a separate passband, to each of the blood flow data signals to produce a bandpass filter (BPF) signal set for each ROI, and wherein the blood pressure training set comprising the BPF signal set for each ROI.

In another aspect, there is provided a system for contactless blood pressure determination of a human subject, the system comprising one or more processors and a data storage device, the one or more processors configured to execute: a transdermal optical imaging (TOI) module to receive a captured image sequence of light re-emitted from the skin of one or more humans, the TOI module determines, using a trained hemoglobin concentration (HC) changes machine learning model trained with a HC changes training set, bit values from a set of bitplanes in the captured image sequence that represent the HC changes of the subject, the HC changes training set comprising the captured image sequence, the TOI module determines a blood flow data signal of one or more predetermined regions of interest (ROIs) of the subject captured on the images based on the bit values from the set of bitplanes that represent the HC changes; a profile module to extract one or more domain knowledge signals associated with the determination of blood pressure from the blood flow data signal of each of the ROIs; a machine learning module to build a trained blood pressure machine learning model with a blood pressure training set, the blood pressure training set comprising the blood flow data signal of the one or more predetermined ROIs and the one or more domain knowledge signals, the machine learning module determines, using the blood pressure machine learning model trained with a blood pressure training set, an estimation of blood pressure of the human subject; and an output module to output the determination of blood pressure.

In a particular case, determination of the estimation of blood pressure by the machine learning module comprises determining an estimation of systolic blood pressure (SBP) and diastolic blood pressure (DBP).

In another case, the set of bitplanes in the captured image sequence that represent the HC changes of the subject are the bitplanes that are determined to significantly increase a signal-to-noise ratio (SNR).

In yet another case, the system further comprising a filter module to preprocess the blood flow data signal with a Butterworth filter or a Chebyshev filter.

In yet another case, extracting the one or more domain knowledge signals by the profile module comprises determining a magnitude profile of the blood flow data signal of each of the ROIs.

In yet another case, determining the magnitude profile by the profile module comprises using digital filters to create a plurality of frequency filtered signals of the blood flow data signal in the time-domain for each image in the captured image sequence.

In yet another case, extracting the one or more domain knowledge signals by the profile module comprises determining a phase profile of the blood flow data signal of each of the ROIs.

In yet another case, determining the phase profile by the profile module comprises: applying a multiplier junction to the phase profile to generate a multiplied phase profile; and applying a low pass filter to the multiplied phase profile to generate a filtered phase profile.

In yet another case, determining the phase profile by the profile module comprises determining a beat profile, the beat profile comprising a plurality of beat signals based on a Doppler or an interference effect.

In yet another case, extracting the one or more domain knowledge signals by the profile module comprises determining at least one of systolic uptake, peak systolic pressure, systolic decline, dicrotic notch, and diastolic runoff of the blood flow data signal of each of the ROIs.

In yet another case, extracting the one or more domain knowledge signals by the profile module comprises determining waveform morphology features of the blood flow data signal of each of the ROIs.

In yet another case, extracting the one or more domain knowledge signals by the profile module comprises determining one or more biosignals, the biosignals comprising at least one of heart rate measured from the human subject, Mayer waves measured from the human subject, and breathing rates measured from the human subject.

In yet another case, the profile module receives ground truth blood pressure data, and wherein the blood pressure training set further comprises the ground truth blood pressure data.

In yet another case, the ground truth blood pressure data comprises at least one of an intra-arterial blood pressure measurement of the human subject, an auscultatory measurement of the human subject, or an oscillometric measurement of the human subject.

In yet another case, the system further comprising a filter module to apply a plurality of band-pass filters, each having a separate passband, to each of the blood flow data signals to produce a bandpass filter (BPF) signal set for each ROI, and wherein the blood pressure training set comprising the BPF signal set for each ROI.

These and other aspects are contemplated and described herein. It will be appreciated that the foregoing summary sets out representative aspects of systems and methods for the determination of blood pressure to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
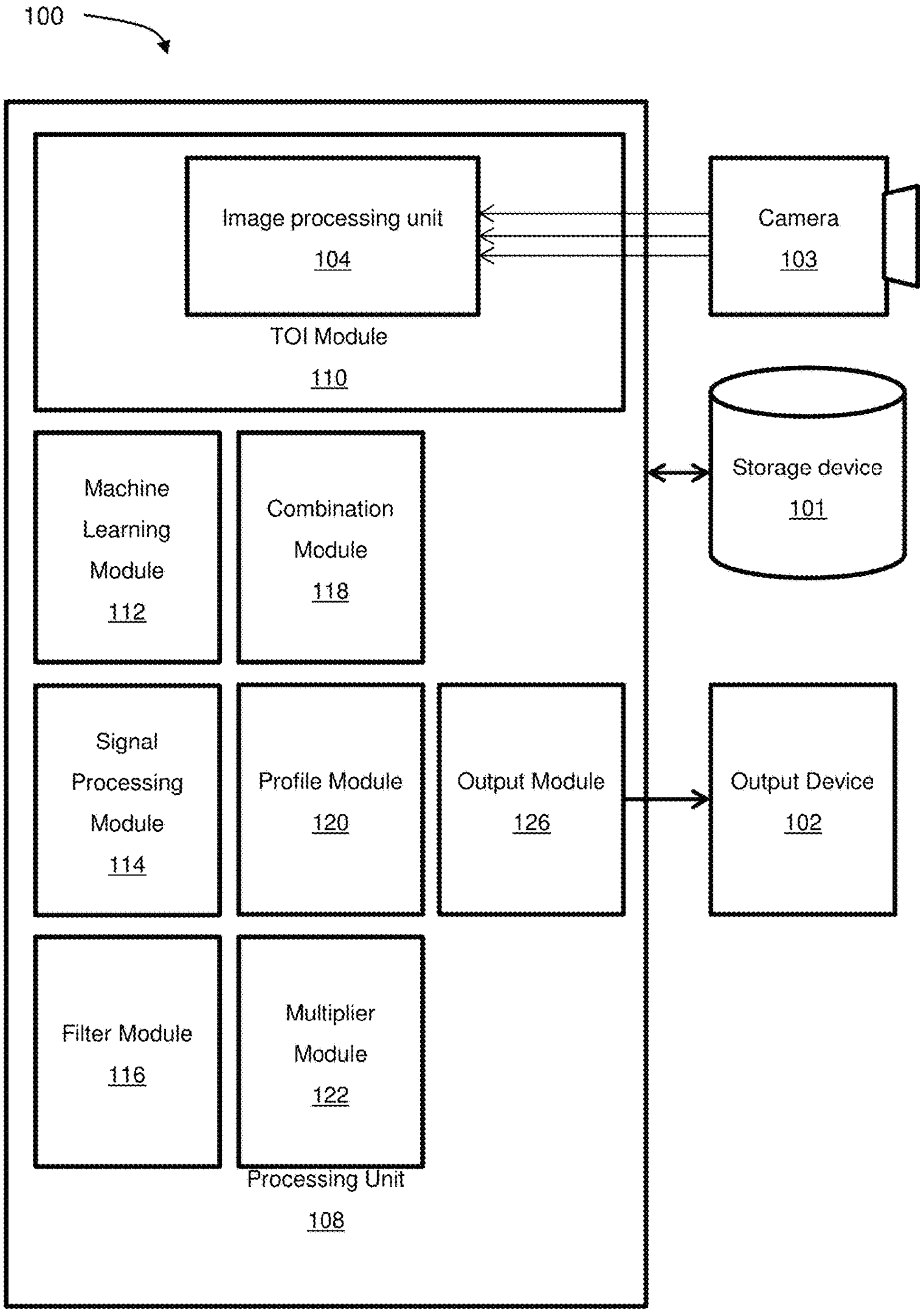
FIG. 1 is an block diagram of a system for contactless blood pressure determination, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to detection of human blood pressure and more specifically to a system and method for contactless human blood pressure determination, via a data-driven and machine learning approach.

In embodiments of the system and method described herein, technical approaches are provided to solve the technological problem of determining human blood pressure without having to contact a human subject by the blood pressure measurement instrument. Blood pressure is determined using image processing techniques performed over a plurality of images captured by one or more digital imaging cameras, such as a digital video camera.

The technical approaches described herein offer the substantial advantages of not requiring direct physical contact between a subject and a blood pressure measurement instrument. As an example of a substantial advantage using the technical approaches described herein, remote blood pressure measurement can be performed on a subject using a suitable imaging device, such as by a video camera communicating over a communications channel. As another example of a substantial advantage using the technical approaches described herein, blood pressure measurements can be determined from previously recorded video material.

The technical approaches described herein also offer the substantial advantages of not requiring periodic recalibration or certification of an instrument. The system and method described herein advantageously do not make use of any moving components such as a pump or an expanding arm cuff and bladder, which typically require recalibration or certification.

The technical approaches described herein advantageously utilize body specific data driven machine-trained models that are executed against an incoming video stream. In some cases, the incoming video stream are a series of images of the subject's facial area. In other cases, the incoming video stream can be a series of images of any body extremity with exposed vascular surface area; for example, the subject's palm. In most cases, each captured body extremity requires separately trained models. For the purposes of the following disclosure, reference will be made to capturing the subject's face with the camera; however, it will be noted that other areas can be used with the techniques described herein.

Referring now to FIG. 1, a system for contactless blood pressure determination 100 is shown. The system 100 includes a processing unit 108, one or more video-cameras 103, a storage device 101, and an output device 102. The processing unit 108 may be communicatively linked to the storage device 101, which may be preloaded, periodically loaded, and/or continuously loaded with video imaging data obtained from one or more video-cameras 103. The processing unit 108 includes various interconnected elements and modules, including a TOI module 110, a machine learning module 112, a signal processing module 114, a first filter module 116, a combination module 118, a profile module 120, a multiplier module 122, and an output module 126. The TOI module includes an image processing unit 104. The video images captured by the video-camera 103 can be processed by the image processing unit 104 and stored on the storage device 101. In further embodiments, one or more of the modules can be executed on separate processing units or devices, including the video-camera 103 or output device 102. In further embodiments, some of the features of the modules may be combined or run on other modules as required.

In some cases, the processing unit 108 can be located on a computing device that is remote from the one or more video-cameras 103 and/or the output device 102, and linked over an appropriate networking architecture; for example, a local-area network (LAN), a wide-area network (WAN), the Internet, or the like. In some cases, the processing unit 108 can be executed on a centralized computer server, such as in off-line batch processing.

The term "video", as used herein, can include sets of still images. Thus, "video camera" can include a camera that captures a sequence of still images and "imaging camera" can include a camera that captures a series of images representing a video stream.

Figure 3:
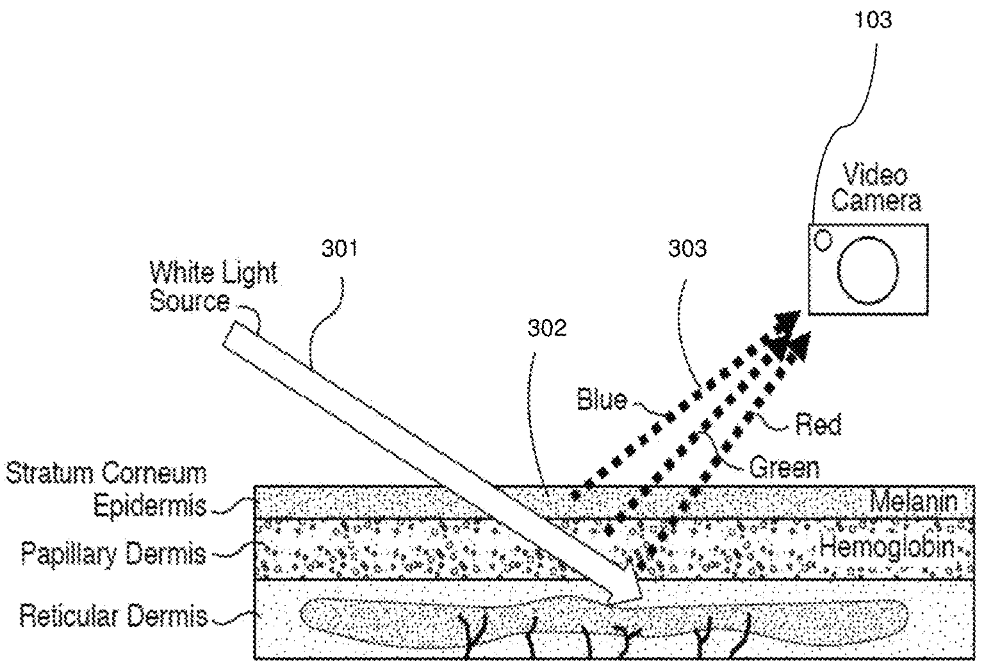
FIG. 3 illustrates re-emission of light from skin epidermal and subdermal layers.
Figure 4:
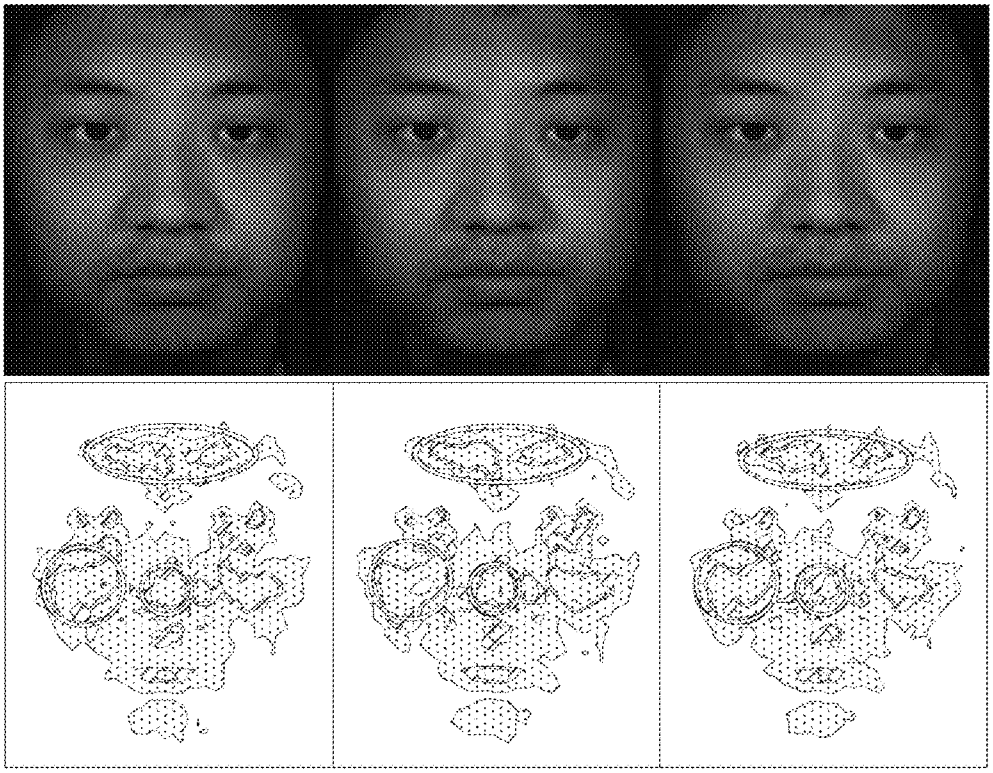
FIG. 4 is a set of surface and corresponding transdermal images illustrating change in hemoglobin concentration for a particular human subject at a particular point in time.

Using transdermal optical imaging (TOI), the TOI module 110 can isolate hemoglobin concentration (HC) from raw images taken from the digital camera 103. Referring now to FIG. 3, a diagram illustrating the re-emission of light from skin is shown. Light 301 travels beneath the skin 302, and re-emits 303 after travelling through different skin tissues. The re-emitted light 303 may then be captured by optical cameras 103. The dominant chromophores affecting the re-emitted light are melanin and hemoglobin. Since melanin and hemoglobin have different color signatures, it has been found that it is possible to obtain images mainly reflecting HC under the epidermis as shown in FIG. 4.

Using transdermal optical imaging (TOI), the TOI module 110, via the image processing unit 104, obtains each captured image in a video stream, from the camera 103, and performs operations upon the image to generate a corresponding optimized hemoglobin concentration (HC) image of the subject. From the HC data, the facial blood flow localized volume concentrations can be determined. The image processing unit 104 isolates HC in the captured video sequence. In an exemplary embodiment, the images of the subject's faces are taken at 30 frames per second using a digital camera 103. It will be appreciated that this process may be performed with alternative digital cameras, lighting conditions, and frame rates.

In a particular case, isolating HC can be accomplished by analyzing bitplanes in the sequence of video images to determine and isolate a set of the bitplanes that approximately maximize signal to noise ratio (SNR). The determination of high SNR bitplanes is made with reference to a first training set of images constituting the captured video sequence, in conjunction with blood pressure data gathered from the human subjects. The determination of high SNR bitplanes is made with reference to an HC training set constituting the captured video sequence. In some cases, this data is supplied along with other devices, for example, EKG, pneumatic respiration, blood pressure, laser Doppler data, or the like, collected from the human subjects, and received by the profile module 120, in order to provide ground truth to train the training set for HC change determination. A blood pressure training data set can consist of blood pressure data obtained from human subjects by using one or more blood pressure measurement devices as ground truth data; for example, an intra-arterial blood pressure measurement approach, an auscultatory approach, or an oscillometric approach. The selection of the training data set based on one of these three exemplary approaches depends on a setting in which the contactless blood pressure measurement system is used; as an example, if the human subject is in a hospital intensive care setting, the training data can be received from an intra-arterial blood pressure measurement approach.

Figure 9:
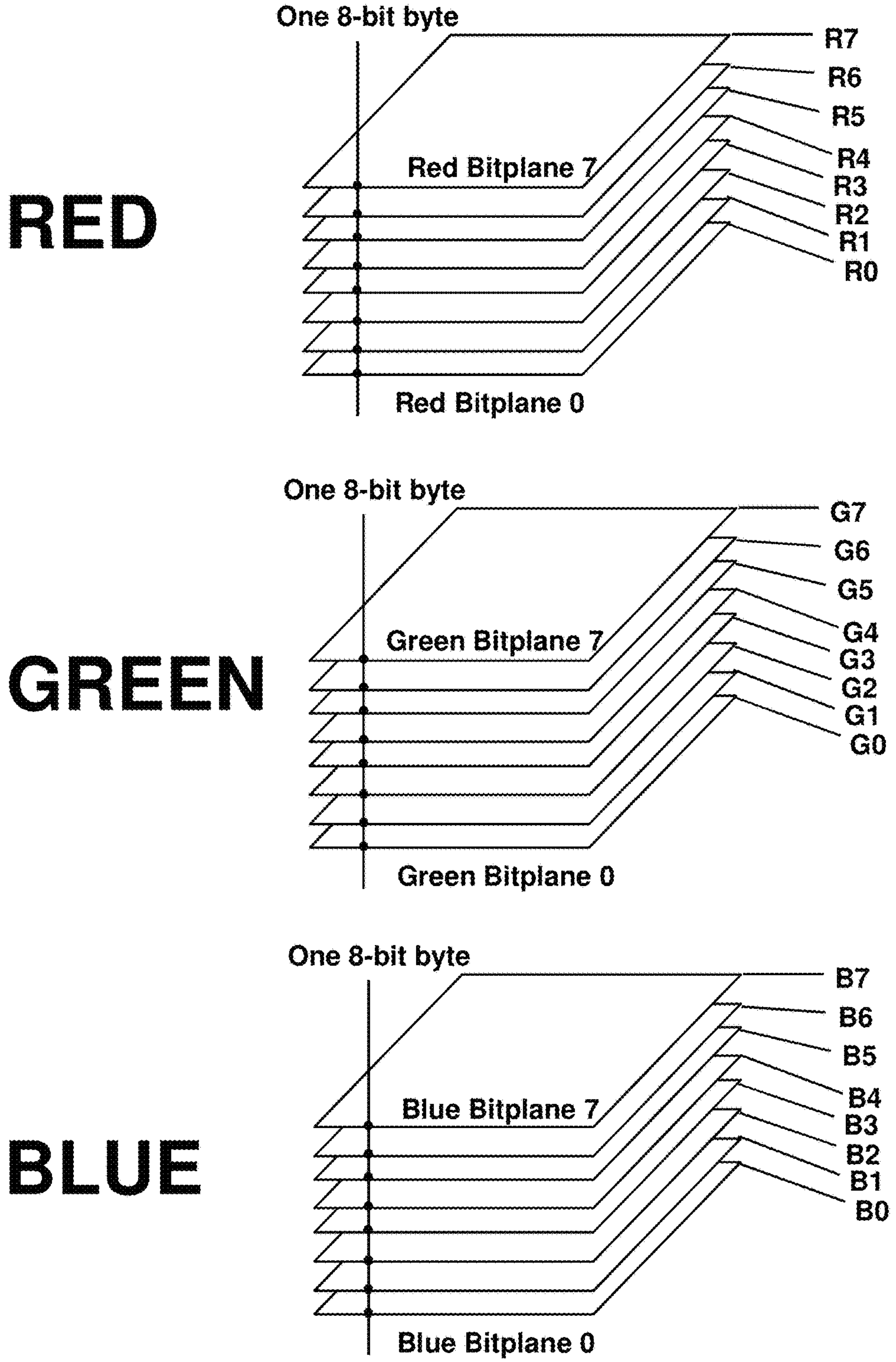
FIG. 9 is an illustration of bitplanes for a three channel image.

Bitplanes are a fundamental aspect of digital images. Typically, a digital image consists of certain number of pixels (for example, a width×height of 1920×1080 pixels). Each pixel of the digital image having one or more channels (for example, color channels red, green, and blue (RGB)). Each channel having a dynamic range, typically 8 bits per pixel per channel, but occasionally 10 bits per pixel per channel for high dynamic range images. Whereby, an array of such bits makes up what is known as the bitplane. In an example, for each image of color videos, there can be three channels (for example, red, green, and blue (RGB)) with 8 bits per channel. Thus, for each pixel of a color image, there are typically 24 layers with 1 bit per layer. A bitplane in such a case is a view of a single 1-bit map of a particular layer of the image across all pixels. For this type of color image, there are therefore typically 24 bitplanes (i.e., a 1-bit image per plane). Hence, for a 1-second color video with 30 frames per second, there are at least 720 (30×24) bitplanes. FIG. 9 is an exemplary illustration of bitplanes for a three-channel image (an image having red, green and blue (RGB) channels). Each stack of layers is multiplied for each channel of the image; for example, as illustrated, there is a stack of bitplanes for each channel in an RGB image. In the embodiments described herein, Applicant recognized the advantages of using bit values for the bitplanes rather than using, for example, merely the averaged values for each channel. Thus, a greater level of accuracy can be achieved for making predictions of HC changes, and thus blood pressure measurements as disclosed herein, and as described for making predictions. Particularly, a greater accuracy is possible because employing bitplanes provides a greater data basis for training the machine learning model.

TOI signals can be taken from regions of interest (ROIs) of the human subject, for example forehead, nose, and cheeks, and can be defined manually or automatically for the video images. The ROIs are preferably non-overlapping. These ROIs are preferably selected on the basis of which HC is particularly indicative of blood pressure measurement. Using the native images that consist of all bitplanes of all three R, G, B channels, signals that change over a particular time period (for example, 10 seconds) on each of the ROIs are extracted.

The raw signals can be pre-processed using one or more filters by the filter module 116, depending on the signal characteristics. Such filters may include, for example, a Butterworth filter, a Chebyshev filter, or the like. Using the filtered signals from two or more ROIs, machine learning is employed to systematically identify bitplanes that will significantly increase the signal differentiation (for example, where the SNR improvement is greater than 0.1 db) and bitplanes that will contribute nothing or decrease the signal differentiation. After discarding the latter, the remaining bitplane images can optimally determine blood flow generally associated with a determination of systolic and diastolic blood pressure.

Machine learning approaches (such as a Long Short Term Memory (LSTM) neural network, or a suitable alternative such as non-linear Support Vector Machine) and deep learning may be used to assess the existence of common spatial-temporal patterns of hemoglobin changes across subjects. The machine learning process involves manipulating the bitplane vectors (for example, 24 bitplanes×30 fps) using the bit value in each pixel of each bitplane along the temporal dimension. In one embodiment, this process requires subtraction and addition of each bitplane to maximize the signal differences in all ROIs over the time period. In some cases, to obtain reliable and robust computational models, the entire dataset can be divided into three sets: the training set (for example, 80% of the whole subject data), the test set (for example, 10% of the whole subject data), and the external validation set (for example, 10% of the whole subject data). The time period can vary depending on the length of the raw data (for example, 15 seconds, 60 seconds, or 120 seconds). The addition or subtraction can be performed in a pixel-wise manner. An existing machine learning algorithm, the Long Short Term Memory (LSTM) neural network, or a suitable alternative thereto is used to efficiently and obtain information about the improvement of differentiation in terms of accuracy, which bitplane(s) contributes the best information, and which does not in terms of feature selection. The Long Short Term Memory (LSTM) neural network allow us to perform group feature selections and classifications. The LSTM machine learning algorithm are discussed in more detail below. From this process, the set of bitplanes to be isolated from image sequences to reflect temporal changes in HC is obtained for determination of blood pressure.

To extract facial blood flow data, facial HC change data on each pixel of each subject's face image is extracted as a function of time when the subject is being viewed by the camera 103. In some cases, to increase signal-to-noise ratio (SNR), the subject's face can be divided into a plurality of regions of interest (ROIs). The division can be according to, for example, the subject's differential underlying physiology, such as by the autonomic nervous system (ANS) regulatory mechanisms. In this way, data in each ROI can be averaged. The ROIs can be manually selected or automatically detected with the use of a face tracking software. The machine learning module 112 can then average the data in each ROI. This information can then form the basis for the training set. As an example, the system 100 can monitor stationary HC changes contained by a selected ROI over time, by observing (or graphing) the resulting temporal profile (for example, shape) of the selected ROI HC intensity values over time. In some cases, the system 100 can monitor more complex migrating HC changes across multiple ROIs by observing (or graphing) the spatial dispersion (HC distribution between ROIs) as it evolves over time.

Thus, it is possible to obtain a video sequence of any subject and apply the HC extracted from selected bitplanes to the computational models to determine blood flow generally associated with systolic and diastolic blood pressure. For long running video streams with changes in blood flow and intensity fluctuations, changes of the estimation and intensity scores over time relying on HC data based on a moving time window (e.g., 10 seconds) may be reported.

Figure 5:
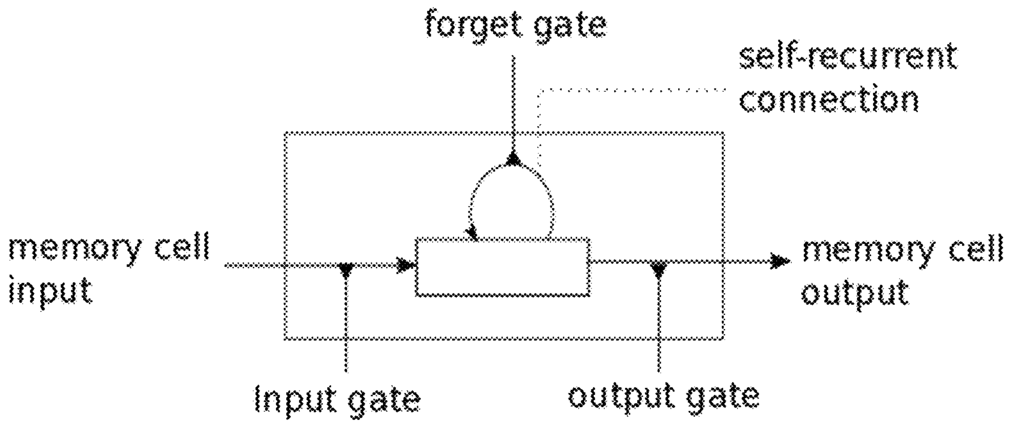
FIG. 5 is a diagrammatic representation of a memory cell.

In an example using the Long Short Term Memory (LSTM) neural network, the LSTM neural network comprises at least three layers of cells. The first layer is an input layer, which accepts the input data. The second (and perhaps additional) layer is a hidden layer, which is composed of memory cells (see FIG. 5). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations:

$x_t$ is the input array to the memory cell layer at time t. In our application, this is the blood flow signal at all ROIs $$\vec{x}_t=[x_{1t}x_{2t} \ldots x_{nt}]$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{C}_t$ the candidate value for the states of the memory cells at time t:

$$i_t=\sigma(W_ix_t+U_ih_{t-1}+b_i)$$

$$\tilde{C}_t=\tanh(W_cx_t+U_ch_{t-1}+b_c)$$

Second, we compute the value for $f_t$, the activation of the memory cells' forget gates at time t:

$$f_t=\sigma(W_fx_t+U_fh_{t-1}+b_f)$$

Given the value of the input gate activation $i_t$, the forget gate activation $f_t$ and the candidate state value $\tilde{C}_t$, we can compute $C_t$ the memory cells' new state at time t:

$$C_t=i_t*\tilde{C}_t+f_t*C_{t-1}$$

With the new state of the memory cells, we can compute the value of their output gates and, subsequently, their outputs:

$$o_f=\sigma(W_ox_t+U_oh_{t-1}+V_oC_t+b_o)$$

$$h_t=o_t*\tanh(C_t)$$

Based on the model of memory cells, for the blood flow distribution at each time step, we can calculate the output from memory cells. Thus, from an input sequence $x_0$, $x_1$, $x_2$, . . . , $x_n$, the memory cells in the LSTM layer will produce a representation sequence $h_0$, $h_1$, $h_2$, . . . , $h_n$.

The goal is to classify the sequence into different conditions. The Logistic Regression output layer generates the probability of each condition based on the representation sequence from the LSTM hidden layer. The vector of the probabilities at time step t can be calculated by:

$$p_t=\text{softmax}(W_{output}h_t+b_{output})$$

where $W_{output}$ is the weight matrix from the hidden layer to the output layer, and $b_{output}$ is the bias vector of the output layer. The condition with the maximum accumulated probability will be the predicted condition of this sequence.

The machine learning module 112 uses the dynamic changes, over time, of localized blood-flow localized volume concentrations at each of the regions-of-interest (ROI) determined by the TOI module 110 to determine blood pressure. The blood pressure measurement approach, used by the machine learning module 112 on the HC change data from the TOI module 110, utilizes a priori generation of specific machine trained computational models combined with the continuous real-time extraction of features from the dynamic observed behaviour of a subject's measured blood flow to produce a predictive estimate of the subject's blood pressure.

The iterative process of machine learning, by the machine learning module 112, allows for the generation of probabilistic mappings or multi-dimensional transfer-functions between the extracted bio-signals presented as training input, as described herein, and the resultant systolic blood pressure (SBP) and diastolic blood pressure (DBP) estimates as the outputs. To train the machine learning module 112, systematic collection of TOI data from a plurality of human subjects, who preferably meet certain stratification criteria for the specific population study, is utilized.

During a machine training cycle, by the machine learning module 112, TOI videos of a plurality of subjects are collected under controlled circumstances and with accompanying "ground truth" information alongside (as described herein). Preferably, the plurality of subjects cover a diverse spectrum of ages, genders, ethnicities, pregnancy, and the like. Preferably, the plurality of subjects have a variety of blood-pressure conditions, from hypotensive to hypertensive. The machine learning models can be trained with increasing robustness as the diversity of the subjects' increases.

The machine learning models are generated according to a supervised training process, where the "ground truth" blood pressure, for both systolic and diastolic data-points, are labelled as a target condition and a variety of training examples are presented in rounds. The training examples are prepared from the subject dataset by the techniques described herein. These techniques utilize advanced data-science machine learning architectures such as Multi-Level Perceptron and Deep (hierarchical) Neural Networks, which are capable of 'deciphering' non-obvious relationships from large datasets to make predictive outcomes. In some cases, the accuracy of the blood pressure estimates from such models is linearly proportional to the quantity and quality of the training dataset.

Figure 2:
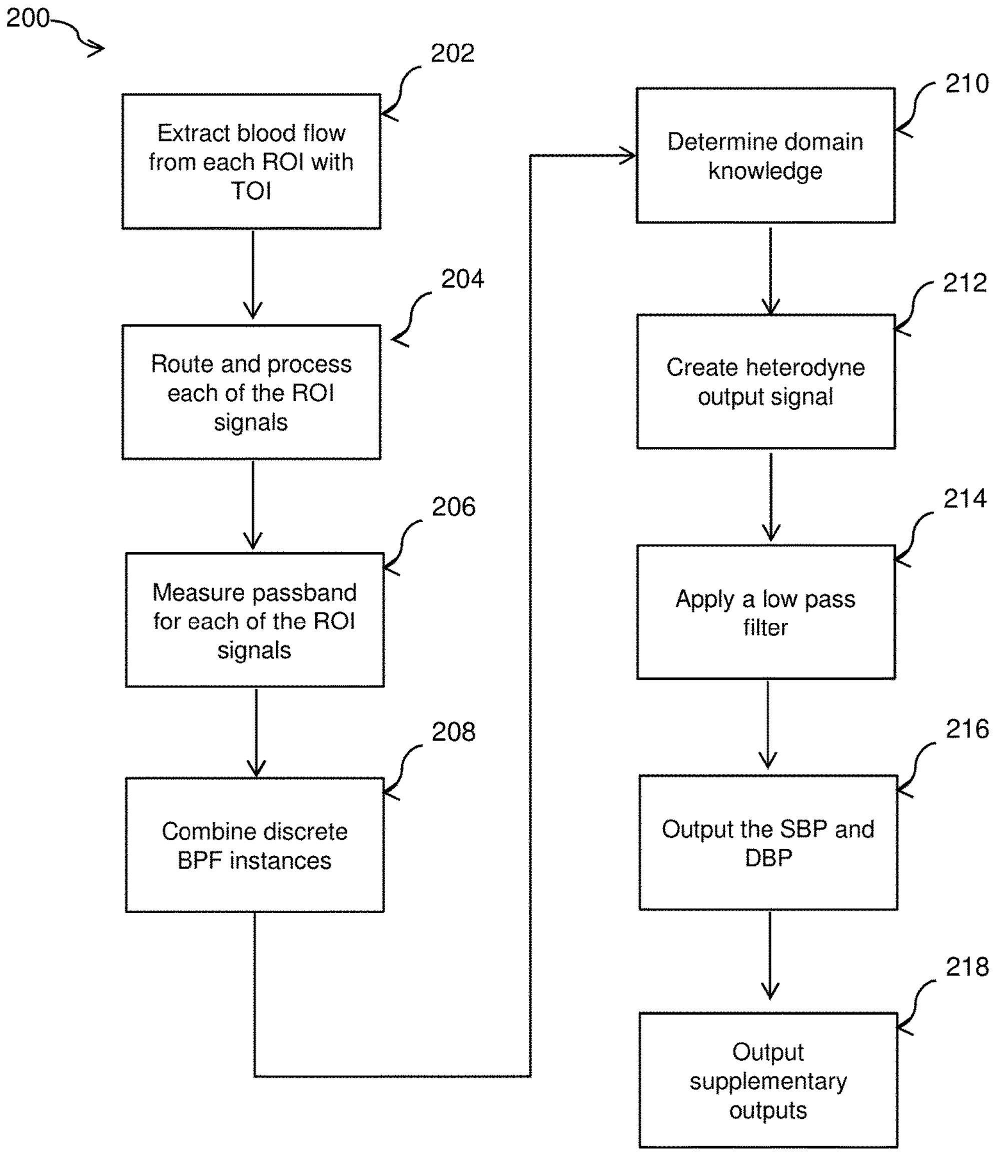
FIG. 2 is a flowchart for a method for contactless blood pressure determination, according to an embodiment.

Turning to FIG. 2, a flowchart for a method for contactless blood pressure determination 200 is shown.

In some cases, for increasing the accuracy of the machine learning model regarding the relationships between blood flow data (as input) and blood pressure estimates (as output), and for reducing the time to arrive at training convergence, the method 200 can leverage domain knowledge to enhance the quality of the input data. Such domain knowledge can include certain attributes, qualities or features of the input data, collected by the profile module 120, that can be consequential to increasing the accuracy of the relationship between the input and the output; for example, systolic rising time, amplitude of systolic peak, amplitude of dicrotic notch, dicrotic notch time, and pulse pressure. Extracting such domain knowledge from the input data and providing it into the machine learning model during an iterative training process, the training of the machine learning model can be exaggerated by the certain attributes, qualities or features, such that the accuracy of the machine learning training can benefit from the inclusion of the domain knowledge. At block 202, facial blood flow is extracted from the video using transdermal optical imaging by the TOI module 110, as described herein, for localized volume concentrations at defined regions-of-interest (ROI) on the face. In addition, the TOI module 110 records dynamic changes of such localized volume concentrations over time.

In an example, the face can be divided into 'm' different regions of interest. In this case, there will be 'm' separate ROI signals, each processing a unique signal extracted from the facial image. The grouping of these 'm' ROI signals is collectively referred to as a bank of ROI signals.

Figure 6:
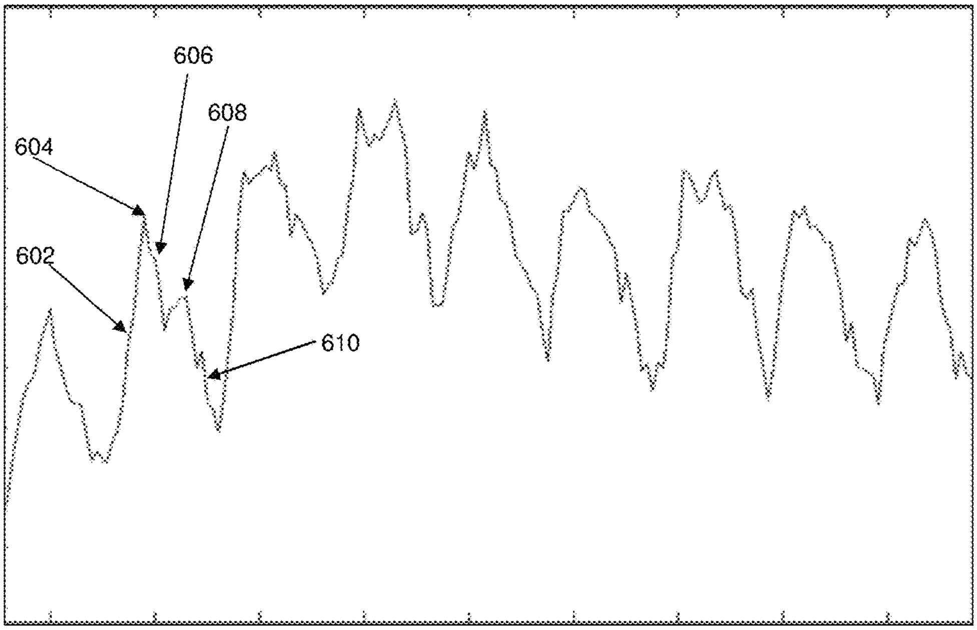
FIG. 6 is graph illustrating an exemplary TOI signal generated by the system of FIG. 1.
Figure 7:
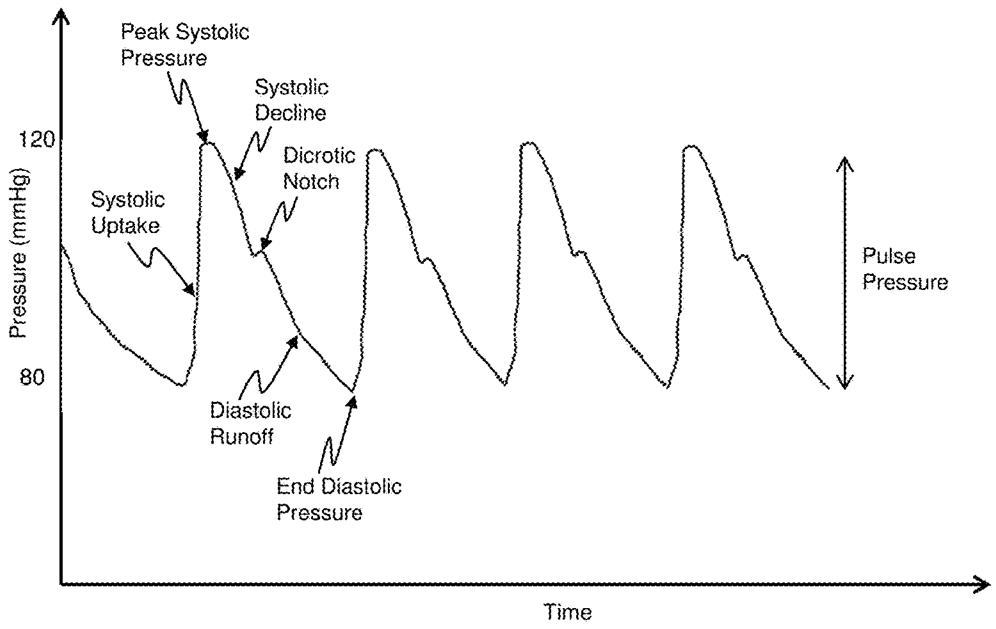
FIG. 7 is a graph illustrating an exemplary arterial pressure signal from a typical inter-arterial blood pressure monitor.

FIG. 6 illustrates an exemplary signal, measured as a function of time, outputted by the TOI module 110 for a particular ROI. As shown, Applicant advantageously recognized that the signal extracted from the TOI module at least partially resembles an exemplary signal taken from an inter-arterial blood pressure monitor, as shown in FIG. 7. In this case, while the TOI signal may be somewhat noisier than the signal extracted from the inter-arterial blood pressure monitor, the pertinent characteristics of the signal can be extracted and thus used to train the machine learning model; for example, characteristics like systolic uptake 602, peak systolic pressure 604, systolic decline 606, dictrotic notch 608, and diastolic runoff 610.

At block 204, the blood-flow volume data from each ROI is processed by the signal processing module 114. The blood-flow volume data from each ROI can be treated as an independent signal and routed through a corresponding processing path. In this way, multiple ROIs each generate signals which are independently, yet concurrently, processed by the signal processing module 114 using digital signal processing (DSP) techniques. The TOI module 110 generates quantity 'm' uniquely defined ROIs superimposed over the facial image, whose boundaries are preferably non-overlapping in area. In other cases, the ROI boundaries may be overlapping.

At block 206, the filter module 116 analyzes 'n' separately defined frequency passbands over the image frequency spectrum received from the signal processing module 114. The spectral energy within each passband is measured by utilizing a narrowband digital filter with 'bandpass' (BPF) characteristics. Each of the resultant bandpass signals is called a "BPF signal" or "BPF instance". In this way, each bandpass filter implements a passband consisting of crisply defined lower and upper frequency specification, where a gain (within the passband range) is preferably much greater than a provided attenuation (outside the passband range).

The filter module 116 constructs each BPF signal as an individual 12th order Elliptical digital filter. Each filter preferably has identical bandpass start/stop and gain/attenuation characteristics, but differing in configured start/stop 'edge' frequencies. The filter module 116 advantageously uses this high-order filter architecture to balance the requirements for a steep roll-off magnitude characteristic with minimal phase distortion. In some cases, the passband 'start' frequency is configurable. In some cases, the passband range (span) is fixed for every BPF at 0.1 Hz; as an example, meaning that the 'end' frequency will be calculated as the 'start' frequency plus 0.1 Hz.

In some cases, at block 208, the combination module 118 combines a set of 'n' discrete BPF instances. In this way, a large contiguous frequency range can be covered by assigning stepwise increasing 'start' frequencies to each BPF instance. Each BPF signal can thus operate on a portion of the facial image available frequency spectrum. Deployment of progressive assignments for the BPF 'start' frequencies can ensure approximately complete coverage of the spectrum; as an example, between 0.1 Hz and 6.0 Hz, with a granularity of 0.1 Hz, yielding a total of 60 BPF instances.

Each ROI signal, of quantity 'm' in total, will have a locally designated BPF set, of quantity 'n' BPF signals in total, to divide and process the frequency spectrum of the ROI signal, as described above. This aggregation of narrowband filters is collectively referred to as the "filter bank".

In some cases, at block 210, the profile module 120 decomposes the ROI signals, acquired across multiple ROIs, to generate a multi-dimensional frequency profile (also called a magnitude profile) and a phase profile (also called a timing profile or velocity profile). The magnitude profile and the timing profile are used as features (input) to the machine learning model by the machine learning module 112. This "feature engineering" can advantageously be used to enhance the effectiveness of the machine learning training process by increasing the useful input data for differentiating blood pressure determinations; and thus, have a higher accuracy at estimating blood pressure.

In the present embodiment, domain knowledge determined by the profile module 120 can include the magnitude profile to enhance an attribute of the blood flow input data. In the case of the magnitude profile, a distribution of frequency information across the blood flow data (per ROI) has been determined by the Applicant to have significance to the estimation of the blood pressure values. As such, as described below, a frequency spectrum analysis per ROI, in this case using fixed banks of digital filters, is performed. The digital filters' signals provide a real-time frequency spectrum of the time-domain signal; comparable to performing fast Fourier transform (FFT) but on every frame. An intended advantage of using digital filters is to create 'n' individual frequency filtered streams that can be manipulated and/or routed independently to build the machine learning model. The analysis is thus then provided to the machine learning model to enhance the accuracy of estimating the blood pressure output values.

In the present embodiment, domain knowledge determined by the profile module 120 can also include the velocity or speed of the blood-flow input data, provided to the machine learning model, for enhancing the accuracy of estimating the blood pressure output values. In a certain case, a beat profile, comprising a collection of beat signals, can be used to quantify the velocity of the blood-flow input data. Beat signals are a motion detection technique based on the Doppler or interference effect. Two beat signals of exactly the same frequency will have zero-hertz (difference) beat signal when multiplied. The frequency of the beat signal is linearly proportional to the 'difference' between the two fundamental signals. In this way, when two arbitrary signals are received and multiplied, the resulting signal will be the difference (subtraction) of the two input frequencies. This difference in frequencies can then be converted to a motion or velocity.

As described, a beat signal can be used to derive an indication of motion of one ROI blood flow signal relative to another ROI blood flow signal; where the frequency of the resultant beat signal is proportional to a difference in blood flow velocity (known as the heterodyne effect). A beat vector can be created for each ROI against some or all of the other ROIs (eliminating any redundant pairs); whereby this collection of beat vectors can be considered the timing profile. In some cases, the timing profile can be constantly updated at fixed intervals. As such, the timing profile can represent an overall complex interference pattern which is based on the differences in blood flow velocities. Therefore the timing profile can be provided to the machine learning model to emphasize blood flow velocity in order to enhance the accuracy of estimating the blood pressure output values.

The magnitude profile includes 'n' discrete points which span the range from the low to the high end of the analyzed spectrum. The magnitude profile is generated by the profile module 120 by creating a single summing junction F(i), where T represents a frequency step or positional index for summation of quantity 'm' total BPF outputs associated with the frequency step 'i'. Each magnitude point, F(i) represents a measure of the narrowband spectral energy summed across 'm' separate ROIs.

The profile module 120 constructs the timing profile 'P' from quantity 's' slices, with each P(s) slice representing the sum of all possible pair combinations of quantity 'm' total BPF outputs associated with the frequency step 'i'. In some cases, the potential pairings are reduced to eliminate redundant combinations.

In some cases, at block 212, the pair combinations, or remaining unique pair combinations, are routed to a multiplier module 122, representing a multiplier junction at index 'k', to create a new 'hetrodyne' output signal H(i, k), which is determined via multiplication of signals from different inputs. For each frequency step 'i', the 'k' index will range through ((m×(m−1))/2) total junctions. P(s) therefore represents the summation of H(i,k) for a given step 'i'. There are quantity 'n' slices of output signals H(i, k) in total to cover the entire spectrum of BPF filters.

In some cases, at block 214, the filter module 116 further processes the 'P' profile by a low pass filter (LPF). In this way, the filter module 116 can remove the sidebands created in the heterodyne alterations while providing a quantifying measure to the 'beat' signal energy resulting from the signal pairings.

In some cases, the machine learning module 112 can utilize selective configurations, such as those configured by a trainer, of the temporal (time changing) features provided by the magnitude profile and the frequency profile to create individually trained model(s), each emphasizing different training characteristics. As described herein, these numerically derived features can also be combined with one or more physiological biosignals that are determined from the TOI blood-flow data; for example, heart-rate, Mayer wave, respiration or breathing cycle, other low or ultra-low frequency arterial oscillations which are naturally occurring and continuously present within the subject, and the like.

Both the features outputted by the filter module 116 and the recovered biosignals (physiological) from the TOI blood-flow can be utilized during the a priori machine training process, as described above, as well as in a posteriori blood pressure estimation, as described herein.

At block 216, the output module 126 outputs, via the trained models of the machine learning module 112, the estimates of systolic blood pressure (SBP) and diastolic blood pressure (DBP) to the output device 102. In some cases, the output module 126, at block 218, can additionally output supplementary outputs to the output device 102. In some cases, the supplementary outputs can be estimated outputs of a mean (average) SBP and a mean (average) DBP. In some cases, the supplementary and independent output can be a pulse pressure (PP) being the difference between SBP and DBP. As an example, these supplementary output values may be used to provide validation points (or limits) for dynamic shifts in the estimates of systolic blood pressure (SBP) and diastolic blood pressure (DBP); such as to differentiate between rapid (acute) changes in the subject's blood pressure versus longer term (chronic) blood pressure measurements.

Accordingly, the method for contactless blood pressure determination 200 uses machine learning to determine estimates of SBP and DBP. The machine learning approach, described herein, of iterative training 'encodes' the complex relationships between the blood flow raw data inputs and the estimated blood pressure outputs. The encoding is of multiple vectors of weights corresponding to the coefficients of salient multi-dimensional transfer functions.

The machine trained models, described herein, use training examples that comprise known inputs (for example, TOI blood flow data) and known outputs (ground truths) of SBP and DBP values. The relationship being approximated by the machine learning model is TOI blood-flow data to SBP and DBP estimates; whereby this relationship is generally complex and multi-dimensional. Through iterative machine learning training, such a relationship can be outputted as vectors of weights and/or coefficients. The trained machine learning model being capable of using such vectors for approximating the input and output relationship between TOI blood flow input and blood pressure estimated output.

In the machine learning models, the magnitude profile F(i) transforms the TOI input data stream into frequency domain values, while (in some cases, concurrently) the timing profile P(i) transforms the same TOI input data stream into a difference, or 'beat', signals between pairs of data streams. In some cases, the magnitude profile F(i) can be generated (transformed) by digital filter banks. In this case, TOI time-series input signals are received and an output is generated into separate frequency 'bins'. The above is referred to as a transform because it is comparable in effect to executing a Fast-Fourier-Transform (FFT) on every single frame. This approach is advantageous because it is much simpler to execute time-domain digital filters, in addition to the fact that it is possible to manipulate or route each output stream independently. In other cases, instead of digital filter banks, the magnitude profile F(i) can be generated using a hardware implementation; for example, using a hardware based field-programmable gate array (FPGA) FFT module. In some cases, the per frame output from a bank of digital filters is comparable to the per frame FFT output of the same digital input signal.

The frequency domain values and the beat signals can be provided to the machine learning model to further refine the model and therefore provide enhanced accuracy for estimating the SBP and DBP.

Figure 8:
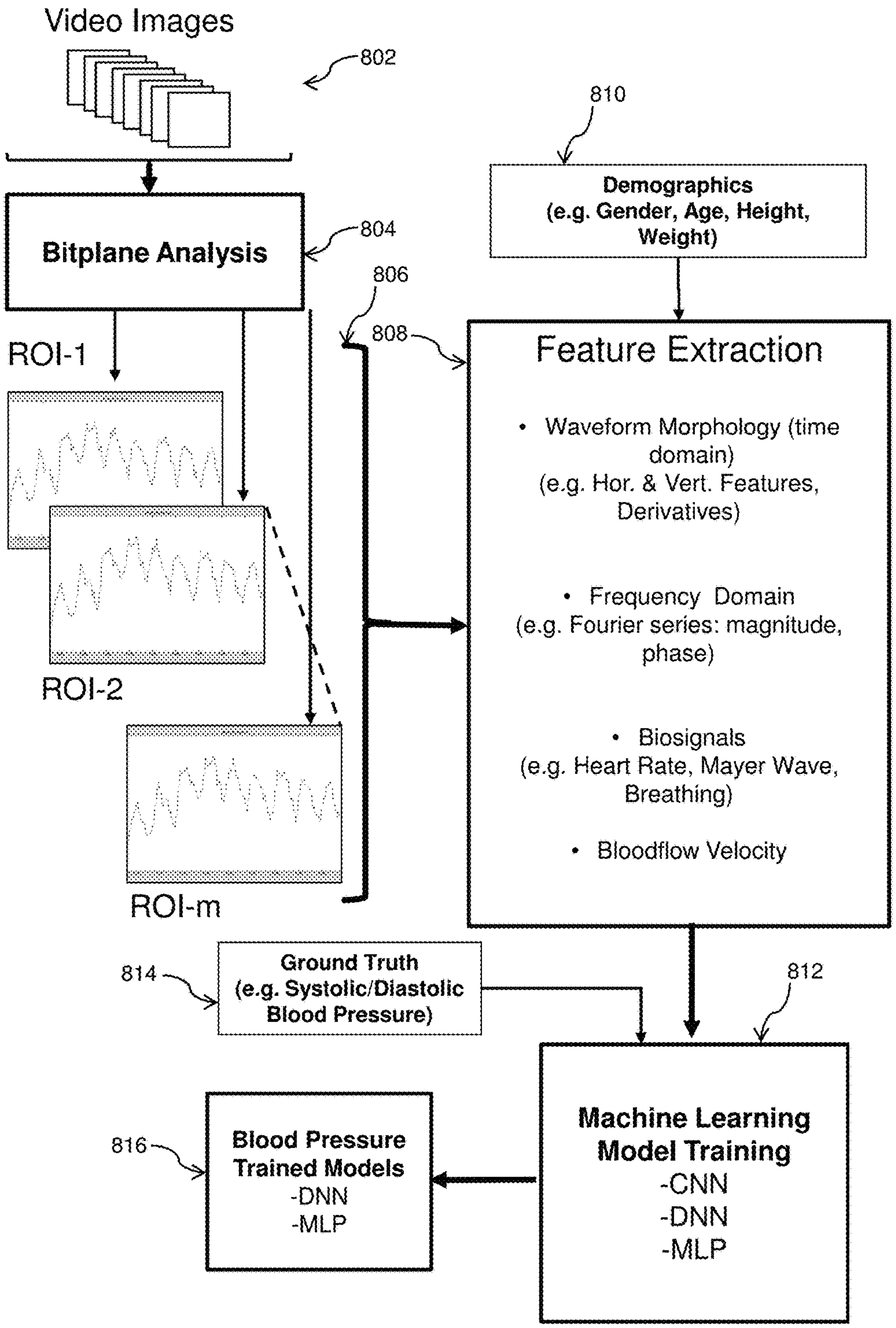
FIG. 8 is a diagrammatic block illustration of the system of FIG. 1.

FIG. 8 illustrates a exemplary diagram of the embodiments described herein. The TOI module 110 receives a set of images 802 of the human subject from a camera. Using machine learning models, the TOI module 110 performs bitplane analysis 804 on the set of images 802 to arrive at TOI signals 806 for each ROI. In some cases, in order to increase accuracy of the blood pressure determination, the TOI module 110 can perform feature extraction 808 on each of the TOI signals for each ROI to feed into the machine learning model, as described herein. Feature extraction 808 can include, for example, determining waveform morphology features of the signals; such as, horizontal (time) and vertical (HC) features of the waves, derivatives of the signals, or the like. Feature extraction 808 can also include, for example, determining frequency domain features of the signals; such as, magnitude and phase of a Fourier series of the signals, or the like. Feature extraction 808 can also include, for example, determining physiological biosignal features of the signals; such as, heart rate, Mayer wave, breathing, or the like. Feature extraction 808 can also include, for example, determining blood-flow velocity based on the signals. In some cases, demographics 810 (for example, gender, age, height, weight, or the like) of the human subjects can be used to inform the feature extraction 808. A machine learning model can then be trained 812 by the machine learning module 112 based on the bitplane data per ROI 806, in some cases in conjunction with the feature extraction 808, to determine blood pressure data. The machine learning model can be, for example, a convolutional neural network (CNN), a deep neural network (DNN), a multilayer perceptron (MLP), or the like. In some cases, the accuracy of the training can be aided by ground truth data 814; such as, systolic/diastolic blood pressure measured on the human training subjects using, for example, an inter-arterial blood pressure monitor. Using the trained machine learning model, blood pressure can be determined for a particular human subject 816.

In further embodiments, optical sensors pointing, or directly attached to the skin of any body parts such as for example the wrist or forehead, in the form of a wrist watch, wrist band, hand band, clothing, footwear, glasses or steering wheel may be used. From these body areas, the system may also extract blood flow data for determination of blood pressure.

In still further embodiments, the system may be installed in robots and their variables (e.g., androids, humanoids) that interact with humans to enable the robots to detect blood pressure on the face or other-body parts of humans whom the robots are interacting with. Thus, the robots equipped with transdermal optical imaging capacities read the humans' blood pressure to enhance machine-human interaction.

The foregoing system and method may be applied to a plurality of fields. In one embodiment the system may be installed in a smartphone device to allow a user of the smartphone to measure their blood pressure. In another embodiment, the system may be provided in a video camera located in a hospital room to allow the hospital staff to monitor the blood pressure of a patient without causing the patient discomfort by having to attach a device to the patient.

Further embodiments can be used in police stations and border stations to monitor the blood pressure of suspects during interrogation. In yet further embodiments, the system can be used in marketing to see the blood pressure changes of consumers when confronted with specific consumer goods.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for contactless blood pressure determination of a human subject, the method executed on one or more processors, the method comprising:

receiving a captured image sequence of light re-emitted from the skin of one or more humans;

determining, using a trained hemoglobin concentration (HC) changes machine learning model trained with a HC changes training set, bit values from a set of bitplanes in the captured image sequence that represent the HC changes of the subject, the HC changes training set comprising the captured image sequence;

determining a blood flow data signal of one or more predetermined regions of interest (ROIs) of the subject captured on the images based on the bit values from the set of bitplanes that represent the HC changes;

applying a plurality of band-pass filters, each having a separate passband, to each of the blood flow data signals to produce a bandpass filter (BPF) signal set for each ROI;

extracting one or more domain knowledge signals associated with the determination of blood pressure from the blood flow data signal of each of the ROIs;

building a trained blood pressure machine learning model with a blood pressure training set, the blood pressure training set comprising the BPF signal set of the one or more predetermined ROIs and the one or more domain knowledge signals;

determining, using the blood pressure machine learning model trained with the blood pressure training set, an estimation of blood pressure for the human subject; and outputting the determination of blood pressure.

2. The method of claim 1, wherein determining the estimation of blood pressure comprises determining an estimation of systolic blood pressure (SBP) and diastolic blood pressure (DBP).

3. The method of claim 1, wherein the set of bitplanes in the captured image sequence that represent the HC changes of the subject are the bitplanes that are determined to significantly increase a signal-to-noise ratio (SNR).

4. The method of claim 1, further comprising preprocessing the blood flow data signal with a Butterworth filter or a Chebyshev filter.

5. The method of claim 1, wherein extracting the one or more domain knowledge signals comprises determining a magnitude profile of the blood flow data signal of each of the ROIs.

6. The method of claim 5, wherein determining the magnitude profile comprises using digital filters to create a plurality of frequency filtered signals of the blood flow data signal in the time-domain for each image in the captured image sequence.

7. The method of claim 1, wherein extracting the one or more domain knowledge signals comprises determining a phase profile of the blood flow data signal of each of the ROIs.

8. The method of claim 7, wherein determining the phase profile comprises:

applying a multiplier junction to the phase profile to generate a multiplied phase profile; and applying a low pass filter to the multiplied phase profile to generate a filtered phase profile.

9. The method of claim 7, wherein determining the phase profile comprises determining a beat profile, the beat profile comprising a plurality of beat signals based on a Doppler or an interference effect.

10. The method of claim 1, wherein extracting the one or more domain knowledge signals comprises determining at least one of systolic uptake, peak systolic pressure, systolic decline, dicrotic notch, pulse pressure, and diastolic runoff of the blood flow data signal of each of the ROIs.

11. The method of claim 1, wherein extracting the one or more domain knowledge signals comprises determining waveform morphology features of the blood flow data signal of each of the ROIs.

12. The method of claim 1, wherein extracting the one or more domain knowledge signals comprises determining one or more biosignals, the biosignals comprising at least one of heart rate measured from the human subject, Mayer waves measured from the human subject, and breathing rates measured from the human subject.

13. The method of claim 1, further comprising receiving ground truth blood pressure data, and wherein the blood pressure training set further comprises the ground truth blood pressure data.

14. The method of claim 13, wherein the ground truth blood pressure data comprises at least one of an intra-arterial blood pressure measurement of the human subject, an auscultatory measurement of the human subject, or an oscillometric measurement of the human subject.

15. A system for contactless blood pressure determination of a human subject, the system comprising one or more processors and a data storage device, the one or more processors configured to execute:

a transdermal optical imaging (TOI) module to receive a captured image sequence of light re-emitted from the skin of one or more humans, the TOI module determines, using a trained hemoglobin concentration (HC) changes machine learning model trained with a HC changes training set, bit values from a set of bitplanes in the captured image sequence that represent the HC changes of the subject, the HC changes training set comprising the captured image sequence, the TOI module determines a blood flow data signal of one or more predetermined regions of interest (ROIs) of the subject captured on the images based on the bit values from the set of bitplanes that represent the HC changes;

a profile module to extract one or more domain knowledge signals associated with the determination of blood pressure from the blood flow data signal of each of the ROIs;

a filter module to apply a plurality of band-pass filters, each having a separate passband, to each of the blood flow data signals to produce a bandpass filter (BPF) signal set for each ROI;

a machine learning module to build a trained blood pressure machine learning model with a blood pressure training set, the blood pressure training set comprising the BPF signal set of the one or more predetermined ROIs and the one or more domain knowledge signals, the machine learning module determines, using the blood pressure machine learning model trained with the blood pressure training set, an estimation of blood pressure of the human subject; and an output module to output the determination of blood pressure.

16. The system of claim 15, wherein determination of the estimation of blood pressure by the machine learning module comprises determining an estimation of systolic blood pressure (SBP) and diastolic blood pressure (DBP).

17. The system of claim 15, wherein the set of bitplanes in the captured image sequence that represent the HC changes of the subject are the bitplanes that are determined to significantly increase a signal-to-noise ratio (SNR).

18. The system of claim 15, further comprising a filter module to preprocess the blood flow data signal with a Butterworth filter or a Chebyshev filter.

19. The system of claim 15, wherein extracting the one or more domain knowledge signals by the profile module comprises determining a magnitude profile of the blood flow data signal of each of the ROIs.

20. The system of claim 19, wherein determining the magnitude profile by the profile module comprises using digital filters to create a plurality of frequency filtered signals of the blood flow data signal in the time-domain for each image in the captured image sequence.

21. The system of claim 15, wherein extracting the one or more domain knowledge signals by the profile module comprises determining a phase profile of the blood flow data signal of each of the ROIs.

22. The system of claim 21, wherein determining the phase profile by the profile module comprises:

applying a multiplier junction to the phase profile to generate a multiplied phase profile; and applying a low pass filter to the multiplied phase profile to generate a filtered phase profile.

23. The system of claim 22, wherein determining the phase profile by the profile module comprises determining a beat profile, the beat profile comprising a plurality of beat signals based on a Doppler or an interference effect.

24. The system of claim 15, wherein extracting the one or more domain knowledge signals by the profile module comprises determining at least one of systolic uptake, peak systolic pressure, systolic decline, dicrotic notch, pulse pressure, and diastolic runoff of the blood flow data signal of each of the ROIs.

25. The system of claim 15, wherein extracting the one or more domain knowledge signals by the profile module comprises determining waveform morphology features of the blood flow data signal of each of the ROIs.

26. The system of claim 15, wherein extracting the one or more domain knowledge signals by the profile module comprises determining one or more biosignals, the biosignals comprising at least one of heart rate measured from the human subject, Mayer waves measured from the human subject, and breathing rates measured from the human subject.

27. The system of claim 15, wherein the profile module receives ground truth blood pressure data, and wherein the blood pressure training set further comprises the ground truth blood pressure data.

28. The system of claim 27, wherein the ground truth blood pressure data comprises at least one of an intra-arterial blood pressure measurement of the human subject, an auscultatory measurement of the human subject, or an oscillometric measurement of the human subject.

* * * * *